United States Patent
Stefan et al.

(10) Patent No.: US 11,197,737 B2
(45) Date of Patent: Dec. 14, 2021

(54) CLAMPING DEVICE AND CLAMPING ARRANGEMENT FOR A MEDICAL INSTRUMENT

(71) Applicant: Karl Storz SE & Co. KG, Tuttlingen (DE)

(72) Inventors: Jochen Stefan, Tuttlingen (DE); Sven Grüner, Tuttlingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 102 days.

(21) Appl. No.: 16/422,555

(22) Filed: May 24, 2019

(65) Prior Publication Data

US 2019/0357994 A1   Nov. 28, 2019

(30) Foreign Application Priority Data

May 28, 2018 (DE) .......................... 102018112679.4

(51) Int. Cl.
*A61B 90/57* (2016.01)
*A61B 17/00* (2006.01)

(52) U.S. Cl.
CPC ........ *A61B 90/57* (2016.02); *A61B 17/00234* (2013.01); *A61B 2017/00292* (2013.01); *A61B 2090/571* (2016.02)

(58) Field of Classification Search
USPC ...... 248/651, 656, 214, 218.4, 219.1, 219.3, 248/226.11, 227.3, 227.4, 316.1, 316.2, 248/316.3, 669; 600/229, 227, 228, 231, 600/234; 269/32, 24–27, 55
See application file for complete search history.

(56) References Cited

U.S. PATENT DOCUMENTS

| | | | | |
|---|---|---|---|---|
| 2,928,161 A | * | 3/1960 | Krueger | ................... B41D 5/00 29/21 |
| 3,534,694 A | * | 10/1970 | Karch | ..................... B41F 27/10 101/378 |
| 3,910,538 A | | 10/1975 | Baitella | |
| 4,491,435 A | | 1/1985 | Meier | |

(Continued)

FOREIGN PATENT DOCUMENTS

CH     608874 A5     1/1979
WO  2016160272 A1   10/2016

OTHER PUBLICATIONS

German Search Report Application No. 10 2018 112 679 Completed: Jan. 11, 2019; dated Jan. 16, 2019 9 pages.

(Continued)

*Primary Examiner* — Alfred J Wujciak
(74) *Attorney, Agent, or Firm* — Whitmyer IP Group LLC

(57) ABSTRACT

A clamping device and method for human-medicine or veterinary-medicine applications for the frictionally engaged locking of at least two holding segments, the clamping device has a first holding segment, a second holding segment; a driveable spindle, via which a rotational movement can be converted into an axial longitudinal movement for spindle-locking the second holding segment, and a threaded plate. In this case, the threaded plate can be moved axially in the opposite direction during the spindle movement, wherein, by counter-movement of the threaded plate, at least one wedge body is moveable in a ramp system, in order to clamp the first holding segment.

18 Claims, 7 Drawing Sheets

(56) References Cited

U.S. PATENT DOCUMENTS

| | | | | |
|---|---|---|---|---|
| 5,427,349 | A * | 6/1995 | Obrecht | B21D 28/00 248/188.4 |
| 6,860,877 | B1 * | 3/2005 | Sanchez | A61B 17/12 600/229 |
| 8,701,452 | B2 * | 4/2014 | Foster | E05B 73/0082 70/19 |
| 2018/0180145 | A1 * | 6/2018 | Schwenke | F16H 25/2003 |

OTHER PUBLICATIONS

United Kingdom Search and Examination Report Application No. GB1907144.8 Completed: Nov. 20, 2019 6 Pages.

* cited by examiner

CLAMPING DEVICE AND CLAMPING ARRANGEMENT FOR A MEDICAL INSTRUMENT

TECHNICAL FIELD

The invention relates to a clamping device and a method for the frictionally engaged locking of at least two holding segments, in particular for medical applications.

BACKGROUND

One-armed or multi-armed holding and guiding systems for medical instruments with passive or active guiding using clamping devices are known. In this case, holding systems for the guiding of instruments are advantageous particularly in minimally invasive surgery, in order to relieve a surgeon, assistant or other operator from the tiring work of holding. A clamping device can be employed to lock at least two holding segments or a holding system, in order to hold a surgical instrument or an end effector such as a manipulator, an endoscope, a clamp or the like. Furthermore, mechatronic assistance systems can also be combined with a holding system.

An aim of the invention is to make available an improved clamping device for medical instruments, in particular for minimally invasive surgery.

In particular, the aim is that devices or systems attached to a clamping device can be handled more simply and thus increase user comfort. In this case, instruments attached to the clamping device, when the clamping device is in a released position, are intended to enable the operator or surgeon to have as great a number of degrees of freedom as possible and to preferably enable, in connection with further holding segments, free mobility of the instrument attached to the clamping device. In other words, simple and precise positioning of the attached instrument should be able to take place.

As soon as the clamping device is actively brought into a locked position, it should be possible to generate holding forces which are reliable and as large as possible. A number of degrees of freedom should be able to be clamped by the locking. In this manner, an instrument such as an endoscope can be held in a desired position for a relatively long time without moving, and the safety for medical interventions can thus be improved.

SUMMARY

On the basis of the invention, the disadvantages encountered in the prior art, such as the restricted freedom of movement of conventional mechanical holding systems, are intended to be reduced. Here, an aim is to make several degrees of freedom available, and to require as little interaction as possible by the operator when a clamping device is to be locked or released. One-handed operability of the clamping device when releasing, positioning and locking is preferably intended to be made possible.

These aims are achieved with a clamping device according to the invention and a method for locking with a clamping device according to the features of the independent claims. Preferred configurations of the invention emerge from the subordinate claims which follow the main claim.

According to a first aspect of the invention, a clamping device for human-medicine or veterinary-medicine applications for the frictionally engaged locking of at least two holding segments is provided, comprising a first holding segment, a second holding segment and a driveable spindle, via which a rotational movement can be converted into an axial longitudinal movement for spindle-locking the second holding segment, wherein a threaded plate can be moved in the opposite direction during the spindle movement, and wherein, by means of the counter-movement of the threaded plate, at least one wedge body is moveable in a ramp system, in order to clamp the first holding segment.

In this manner, it is possible for a plurality of holding segments or degrees of freedom to be clamped with the aid of only a single driveable component of the clamping device i.e. with the aid of the spindle, and for the clamping or locking with a single drive unit to be guaranteed. The first holding segment can be designed as a perpendicular base column, which can be affixed to a standard rail of an operating table, for example. The second holding segment can have one or more arm segments and be locked by the axial spindle movement in the distal direction.

According to a further aspect of the invention, a housing is pivotably borne around a transverse axis and around the axis of the first holding segment.

In this manner, a base joint or a so-called shoulder joint is made available, which on the one hand is rotatably borne on the first holding segment and on the other hand is rotatably connected to the housing of the clamping device. Both degrees of freedom can be clamped with the aid of the ramp system of the clamping device.

According to a further aspect of the invention, the threaded plate is arranged axially concentric with the spindle and has an inner thread which is mutually engaged with an outer thread of the spindle for displacement in the axial direction.

In this manner, the counter-bearing force of the spindle can be effectively used to move the threaded plate in the proximal direction and then to clamp the first holding segment or the base joint. Through the axially concentric arrangement of the threaded plate and spindle, the clamping device can be constructed in a space-saving manner.

According to a further aspect of the invention, the interengaging threads of the spindle and of the threaded plate are designed as a trapezoidal thread.

The trapezoidal thread can advantageously be used to transmit the spindle movement. In contrast to thread pitches with a triangular profile, for example, the trapezoidal thread possesses larger slopes, as a result of which the self-inhibition can be advantageously reduced.

According to a further aspect of the invention, the ramp system has at least one ramp loop which is penetrated centrally by the spindle and which has at least one ramp, in order to move the at least one wedge body laterally with respect to the spindle axis.

The ramp, in conjunction with the wedge body, can divert the counter-forces of the spindle laterally, i.e. deflect them by approximately 90°.

According to a further aspect of the invention, the clamping device has a locking unit which interacts with the ramp system, for the clamping of the first holding segment, wherein the locking unit has a tightening screw, which can be moved transversely to the spindle axis by means of the ramp system, and a cross-hole bolt which guides the first holding segment.

With the aid of the tightening screw, the lateral force can be transmitted onto the cross-hole bolt, by the preferably perpendicularly arranged holding segment or the base column being mounted.

According to a further aspect of the invention, the ramp loop can be supported on one side by a support arranged in a stationary manner in a housing, in order to pull the cross-hole bolt, for the clamping of the first holding segment, to the housing, or to push it away therefrom, by means of the tightening screw.

If the first holding segment or the base column is pulled to the housing via the cross-hole bolt, the first holding segment can be clamped with only a few intermediate links. Alternatively, by providing more intermediate links, the mode of operation can also be reversed and the first holding segment for clamping can be pushed away from the housing.

According to a further aspect of the invention, the ramp loop has respectively on two opposing sides, at least one ramp for interacting with assignable wedge bodies, in order to form two opposing ramp/mating-ramp systems.

In this manner, one wedge body respectively is arranged on both sides of the spindle, so that the ramp loop does not experience any stress on one side when force is deflected. In other words, due to the two wedge bodies which are arranged symmetrical with respect to one another, the assignable ramp surfaces can be acted upon by the same force component respectively on both sides of the ramp loop and a low-friction lateral movement of the ramp loop is supported.

According to a further aspect of the invention, the at least one ramp and at least one mating ramp engage one another with the assignable wedge surfaces of a wedge body, this engagement being brought about by a multiplicity of sliding bodies.

The sliding bodies can advantageously reduce the friction and lead to better effectiveness. The effectiveness can be over 90%.

According to a further aspect of the invention, the sliding bodies are rolling bodies in the form of spheres, cylinder rollers or barrel rollers.

As a result, the wedge body can be moved with low friction. The number of rolling bodies can be varied, so that the stress when forces are transmitted can be distributed over a plurality of rolling bodies. The arched running surface of barrel rollers can advantageously be used for automatic centering.

According to a further aspect of the invention, the at least one ramp and/or mating ramp have curved tracks for the sliding bodies.

Curved tracks can serve to support automatic centering of the sliding bodies. Through the use of sliding or rolling bodies in curved tracks it is not only possible to reduce the friction, but also costs and construction space can be reduced.

According to a further aspect of the invention, the at least one ramp and mating ramp directly engage in a sliding manner with the assignable wedge surfaces of the wedge body.

In this manner, it is possible to dispense with the sliding bodies and the production costs are reduced through simpler assembly and reduction of the individual components. However, if simple sliding surfaces are used, i.e. sliding surfaces without the sliding body insert, the friction increases and the effectiveness of the force deflection thus falls to below 60%.

According to a further aspect of the present invention, the spindle and/or the locking unit has a receptacle for spring means.

The spring means can be used to adjust a residual inhibition. In this manner, the housing or the base joint is, for example, prevented from being able to flap around in an uncontrolled manner in relation to the first holding segment or the base column. Unforeseen movements upon release of the clamping device can thus be reduced.

According to a further aspect of the invention, the spindle can be driven by means of a drive unit, the drive unit being selected from the group comprising an electric motor, a pneumatic drive and a hydraulic drive.

In this manner, the spindle can be operated automatically with a single drive unit. If an electric motor is used, the housing has the associated switching logic, the control unit and power supply (preferably a battery). If there is a failure of the power supply in the clamped state, the clamping device is set up in such a way that, for safety reasons, it also functions mechanically. In other words, since the locking or clamping is based on friction, the holding segments can, in an emergency, still be moved by the application of high external forces. This does not cause any damage to the clamping device. If there were to be a failure of the power supply in the freed state, this state is also maintained. The system requires electrical energy solely to change between the clamped state and the free state. The active state in each case is self-sustaining due to the self-inhibition.

According to a further aspect of the invention, the drive unit comprises an electric motor and the spindle is floatingly mounted, a balancing means being provided between the spindle and the electric motor.

With the aid of a balancing means, such as a sliding square for example, it is possible to compensate an axial offset. For example, an electric motor can, via a balancing means, drive the spindle which is screwed in the distal direction as a result.

According to a further aspect of the invention, the housing has a mounting rail for fitting additional masses.

The housing thus contributes to the reach of the holding segments which can be distally attached to the clamping device. The dead masses of the drive unit, a motor unit and a battery can be adapted to the respective requirements by way of additional fittable masses.

Furthermore, a method for human-medicine or veterinary-medicine applications for the frictionally engaged locking of at least two holding segments is provided, comprising the following method steps: driving a spindle, in order to convert a rotational movement of the spindle into an axial longitudinal movement, wherein the second holding segment is locked by means of a longitudinal movement of the spindle in the distal direction; and by means of the spindle movement, simultaneous moving of a threaded plate in the opposite direction, wherein by means of the counter-movement of the threaded plate in the proximal direction, at least one wedge body is moved in a ramp system for the clamp-locking of the first holding segment.

BRIEF DESCRIPTION OF THE DRAWINGS

Further advantages and features of the invention emerge from the following description of exemplary embodiments with reference to the figures. In the drawings.

The depictions are schematic and are not necessarily true to scale. Furthermore, they do not show all details but rather partly restrict themselves to the depiction of the details which are significant to the invention and of further features which facilitate the explanation and description of the invention. Identical elements in the various figures are labelled with identical reference numbers.

DETAILED DESCRIPTION

Figure 1:
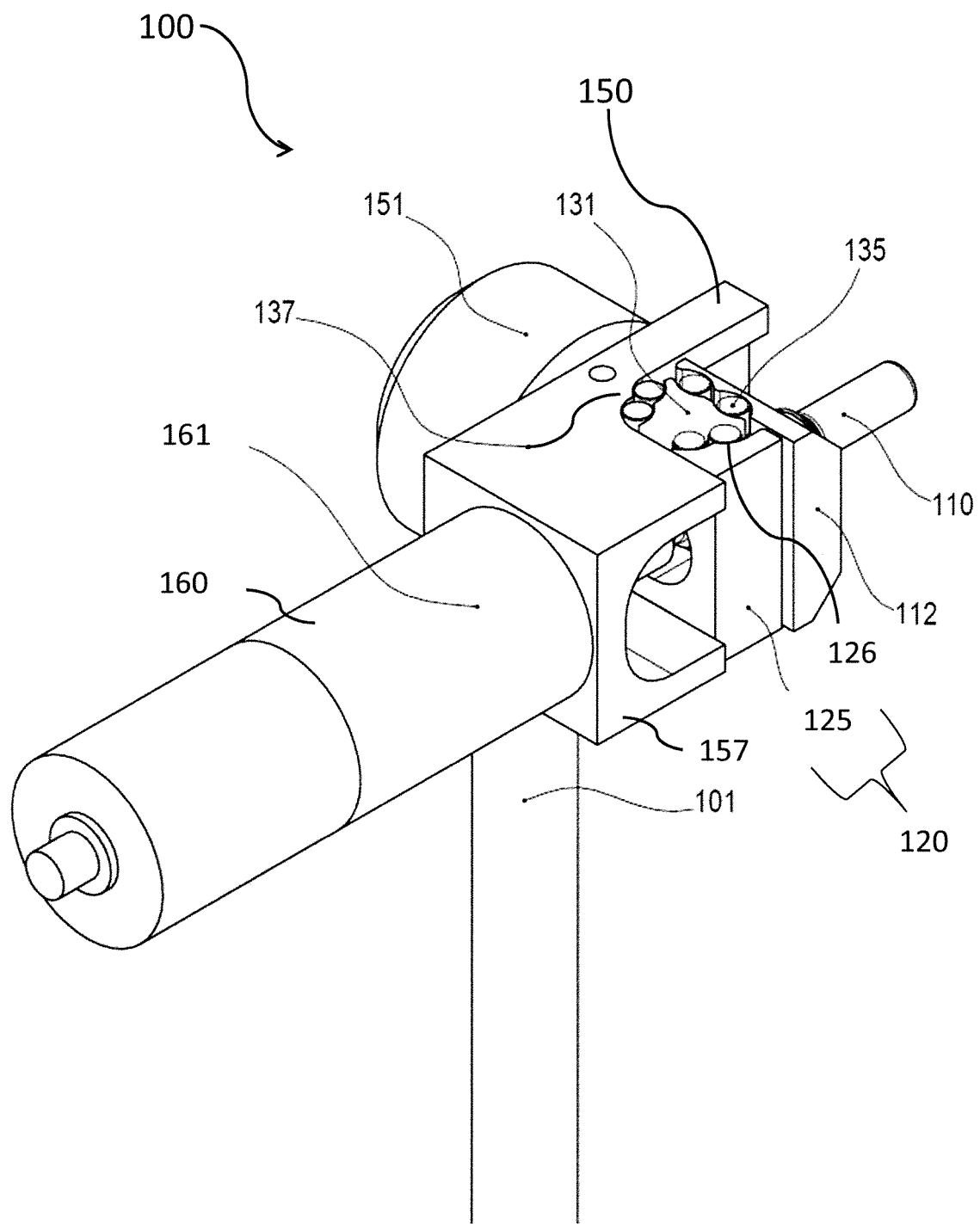
FIG. 1 shows a perspective view of a clamping device according to the invention.

The perspective view from FIG. 1 shows a clamping device 100 according to the invention for medical instruments. This clamping device 100 consists substantially of a first holding segment 101, a spindle 110 and a ramp system 120 for clamping the first holding segment 101. The first holding segment 101 is designed as a perpendicularly arranged base column. A base joint or a so-called shoulder joint connects the holding segment or base column 101 rotatably to the housing. In addition, the housing 150 is borne pivotably around the perpendicular axis of the first holding segment by means of the base joint. Both degrees of freedom can be clamped with the aid of the ramp system 120 of the clamping device 100.

In addition, a second holding segment 102 which is not shown can be clamped by the spindle 110. The spindle 110 can be driven by means of a single drive unit 160 designed as an electric motor 161. Via the driveable spindle 110, a rotational movement can be converted into an axial longitudinal movement in the distal direction to spindle-lock the second holding segment, which is not shown.

The spindle 110 is guided axially concentrically through a threaded plate 112. If the spindle 110 is moved in the distal direction, the threaded plate 112 is also simultaneously moved in the opposite direction i.e. in the proximal direction. By means of the counter-movement of the threaded plate 112, the wedge body 131 can be moved in a ramp system 120. Alongside the wedge body 131, the ramp system 120 has a ramp loop 125 which is centrally penetrated by the spindle 110. The ramp loop 125 has a ramp or ramp surface 126. The wedge body 131 is arranged between the ramp 126 and a mating ramp 137. In this case, the mating ramp 137 is designed as part of a housing component 157 and forms a stationary support surface for the moveable wedge body 131. The ramp 126 of the ramp loop 125 and the mating ramp 137 engage one another with the wedge body 131 through a multiplicity of sliding bodies 135.

That end of the first holding segment 101 located in the column head 151 can be clamped or locked through a spindle movement in the distal direction and the thus generated counter-movement of the threaded plate 112, interacting with the ramp system 120. The following FIGS. 2A and 2B schematically show the locked and released position of the clamping device 100.

Figure 2A:
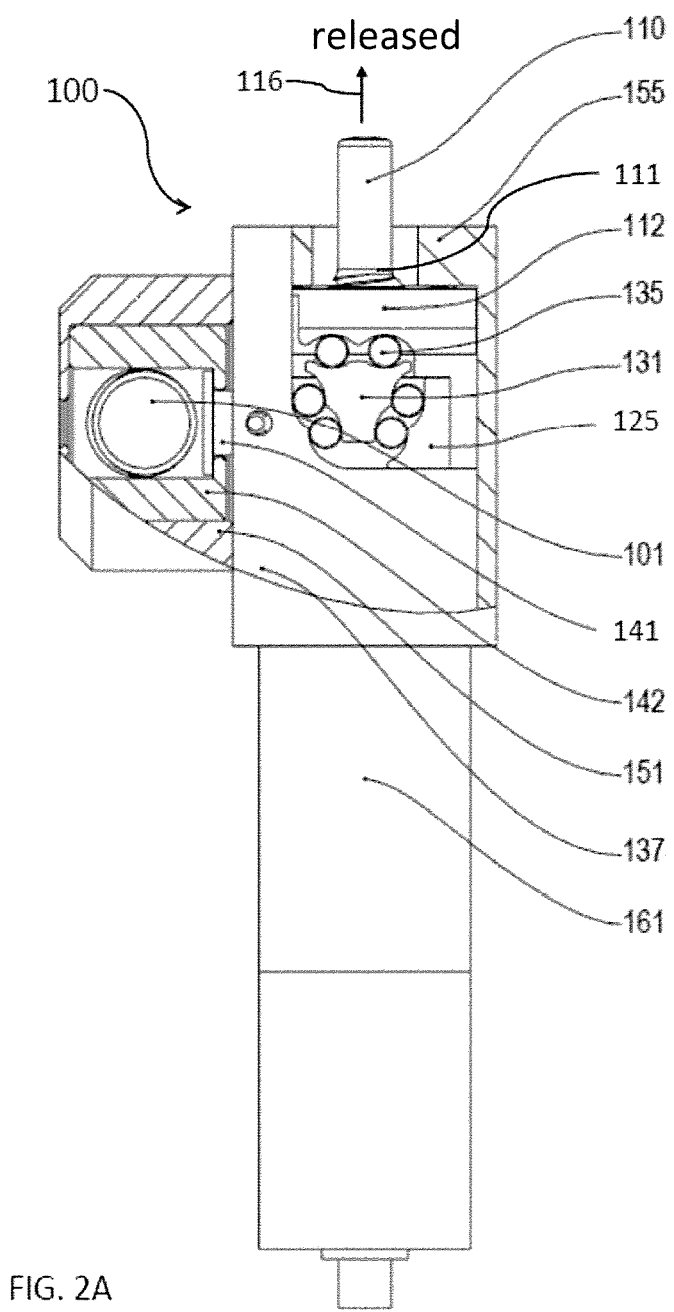
FIG. 2A shows a schematic plan view of the clamping device according to FIG. 1 in the released position.

FIG. 2A shows the released position of the clamping device 100. A shifting of the clamping device 100 from the released position shown in FIG. 2A into the locked position according to FIG. 2B takes place via the axial longitudinal movement in the distal direction, indicated by the arrow 116. In the released position, the outer thread 111 of the spindle protrudes only slightly beyond the threaded plate 112. In this position, the free end of the threaded spindle 110 likewise protrudes minimally beyond the front plate of the housing component 155. In the released position of the spindle 110 (FIG. 2A), a holding segment (not shown in this drawing) attached thereto can be freed.

Figure 2B:
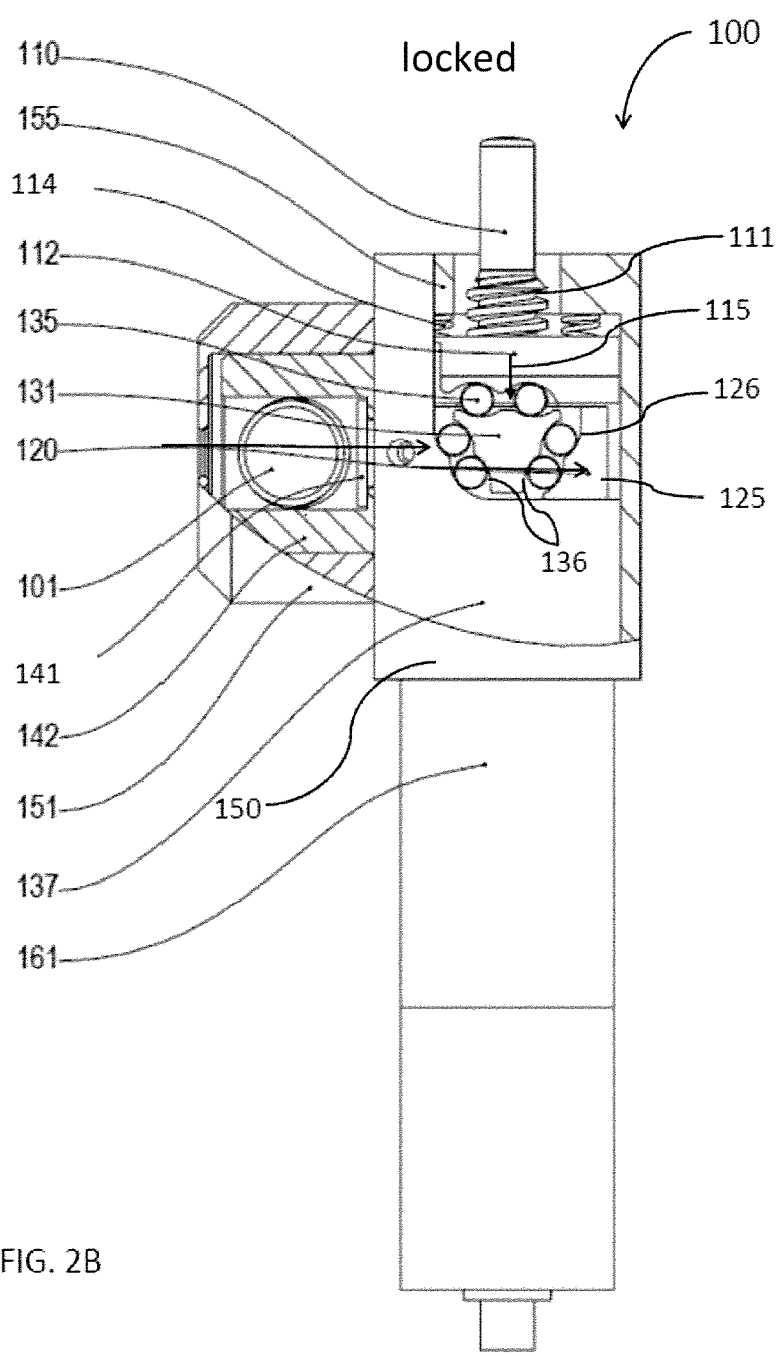
FIG. 2B shows a schematic plan view of the clamping device shown in FIG. 2A, in the locked position.

The drawings FIG. 2A and FIG. 2B show the first holding segment 101 from above. For this purpose, the column head 151 is partly cut off to allow for better visibility. The holding segment 101 is guided in the cross-hole bolt 142. The first holding segment 101 is connected to the ramp system 120 via the tightening screw 141.

The electric motor 161 can be used as a driving force for the spindle 110. In order to go from the released position (FIG. 2A) into the locked position (FIG. 2B), the electric motor 161 drives the threaded spindle 110 in the direction of the arrow 116, i.e. in the distal direction. FIG. 2B shows the position after the spindle 110 has been screwed forwards by the electric motor and has thus assumed the locking position. By means of the axial movement in the distal direction, distal pressure can be built up with the free end of the spindle 110, in order to lock holding segments (not shown here) attached there, so that the spindle end acts as a pressure bolt.

FIG. 2B shows, in comparison with FIG. 2A, that the spindle 112 in an inner thread of the threaded plate has moved in the distal direction, so that the spindle end protrudes further beyond the end of the housing component 155. The inner thread is rearwardly supported by the distal movement of the spindle 110. As a result, a bearing force arises in the opposite direction. The bearing force acts in the direction of the arrow 115 (see FIG. 2B), i.e. in the proximal direction. By means of the bearing force, the threaded plate 112 presses against the sliding body 135, which is configured as a rolling body. The force is transmitted onto the wedge body 131 via the two rolling bodies at the side of the threaded plate 112. The wedge body 131 has wedge surfaces 136 which are oriented inclined relative to one another. Each of the wedge surfaces 136 has a curved track for the sliding bodies 135.

The wedge body 131 is moved by the threaded plate 112 between a ramp 126 of the ramp loop 125 and a stationary support of the housing component 157 through the bearing force. In this case, the wedge body 131 is supported laterally against the housing 150 via the sliding bodies 135. It is advantageous here that the respective counter-forces can be introduced directly into the housing 150. In contrast, the wedge body 131 presses onto the ramp 126 of the ramp loop 125, likewise via two sliding bodies 135. The moveable ramp loop 125 experiences a lateral tensile force as a result. This force is transmitted onto the cross-hole bolt 142 via the tightening screw 141. The first holding segment 101, which is located in the cross-hole bolt 142, can be clamped by this force. In the locked position, the first holding segment is pulled by the cross-hole bolt 142 to the housing 150, and in the process the column head 151 is pressed and clamped onto the housing wall, in such a way that the housing 150 can no longer be turned in relation to the holding segment 101 or the holding segment 101 can no longer be turned in relation to the housing 150.

By means of the ramp system 120, it is possible to deflect the bearing force of the spindle 110 laterally, i.e. by 90°. The sliding bodies 135 advantageously reduce the friction here and lead to better effectiveness. Rolling bodies in the form of spheres, cylinder rollers or barrel rollers can be used as sliding bodies 135. Through the use of said rolling bodies, the effectiveness can be raised to over 90%.

Figure 3:
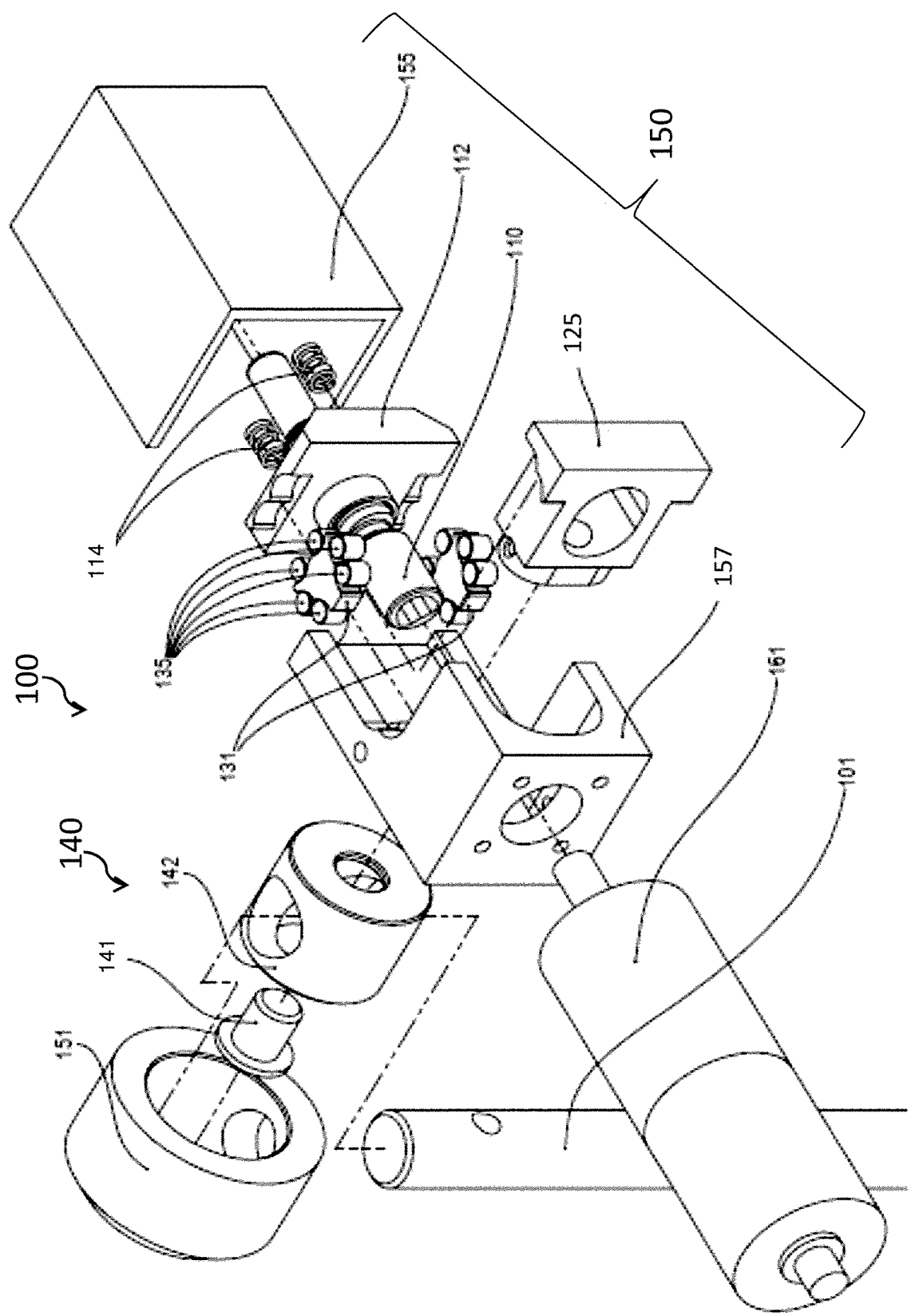
FIG. 3 shows a perspective exploded view of an inventive clamping device according to FIGS. 1 and 2A-2B.

FIG. 3 shows an exploded depiction of the clamping device 100. The ramp system 120 with the threaded spindle 110 is surrounded by a housing 150. FIG. 3 shows that the wedge body 131 with the sliding bodies (6 in total here, i.e. 2 per wedge surface) is located mirror-symmetrically also under the spindle 110.

The housing 150 consists of a multiplicity of components. The housing component 155, which has a front plate, and the housing component 157, which has the mating ramp 137, is shown here at the distal end. Through an outer wall of the housing component 157, a connecting member can be guided to the drive unit 160 comprising an electric motor 161. The spindle 110 and the threaded plate 112 can both be floatingly mounted, in order thus to be able to move vis-à-vis the housing 150 and the housing components 157 and 155. Through suitable balancing means (not shown here) between the spindle 110 and the electric motor 161, it is possible to compensate an axial offset when transmitting the torque from the electric motor 161. By means of an assigned actuation element or actuator not shown here, the electric motor 161 can be activated to rotate the spindle 110.

The housing or housing arrangement 150, with the drive unit 160, is connected to the first holding segment 101 via the tightening screw 141 and the cross-hole bolt 142. The housing 150 with the drive unit 160 can in this manner be pivoted relative to the first holding segment 101. For low-friction pivotability or rotatability, a sliding disc (not shown here) can be supplied at that side of the cross-hole bolt 142 which faces the housing 150 or housing component 157. A diamond carbon disc is preferably used for the sliding disc.

For use and applications in veterinary medicine or human medicine, the first holding segment 101 is arranged perpendicularly and affixed to an operating table, for example. The end of the first holding segment 101, and the cross-hole bolt 142, is concealed by the column head 151. In use, both the housing 150 with the drive unit 160 and also the first holding segment 101 are covered by a sterile cover or drape.

In order for there to still be a certain residual inhibition when the clamping device 100 is in the released position, spring means 114 are made available. In this manner, it is possible to prevent holding segments, which can be attached to the distal end of the clamping device, from flapping around in an uncontrolled manner when in the released position, or rather to prevent the housing from rotating too abruptly and thus in an uncontrolled manner relative to the first holding segment 101 in the event of the locking being released. No distally attached holding segments are shown in this depiction from FIG. 3. It is possible, for example, for at least two holding segments to be attached, which form an arm-like holding device with a central joint (see reference number 20 in FIG. 5). The spring means 114 operatively connected to the spindle 110 can be used advantageously in order to avoid a completely released flappy holding device 20 or arm in the released position.

Figure 4:
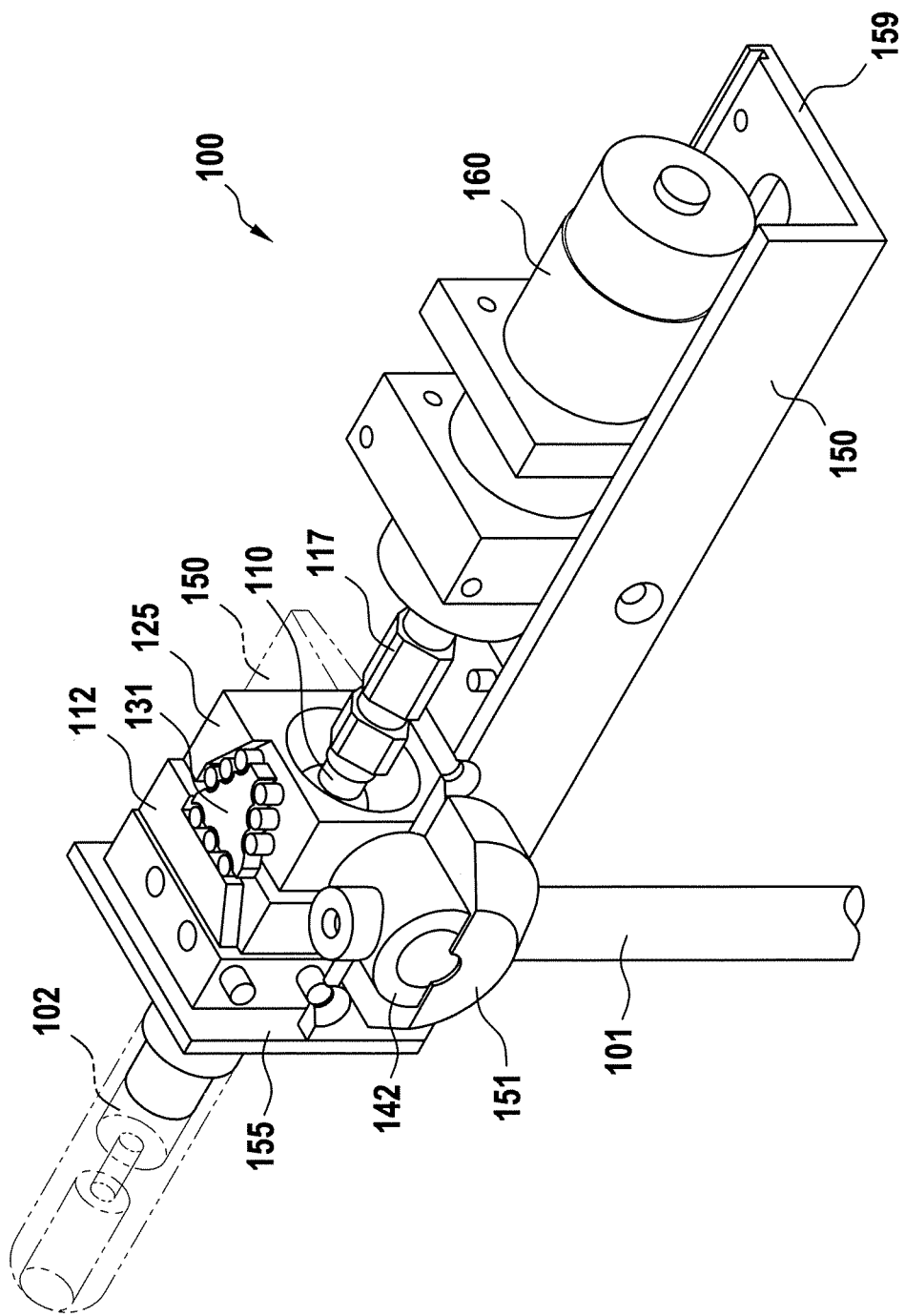
FIG. 4 shows a perspective view of a further embodiment of the clamping device according to the invention, with components which are depicted partly transparently.

FIG. 4 shows a further embodiment of the invention, with identical elements being shown with identical reference numbers. In addition to the preceding figures, this drawing has a partial outline of a second holding segment 102. Furthermore, the depicted embodiment additionally shows a sliding square 117, which connects the drive unit 160 to the spindle 110 which is only partly shown. The drive unit 160 is positioned in a housing channel 159.

The embodiment shown in FIG. 4 is substantially constructed like the embodiment from FIG. 1, with parts of a second holding segment 102 also being shown here alongside the first holding segment 101. A thrust rod is arranged in the holding segment 102, with this thrust rod, with the pressure bolt located at the free end of the spindle 110, being able to be shifted along the longitudinal axis for clamping.

Furthermore, a coupling element or a coupling device for connecting the second holding segment 102 is indicated in FIG. 4. Instead of a coupling, it is also possible for the second holding segment to be integrally connected to the housing 150 of the clamping device. In the case of this design too, a thrust rod arranged axially in the second holding segment 102 can be shifted along the longitudinal axis with the spindle 110 to clamp further holding segments and/or joints.

FIG. 4 shows a ramp system according to the structure, in principle, as already described in FIGS. 1 to 3. The wedge body 131 differs from the wedge body in the preceding embodiments substantially in that three rolling bodies are arranged at each of the three wedge surfaces. Furthermore, the wedge surfaces each have corresponding curved tracks for optimal centering for the rolling bodies.

The housing 150 of the clamping device from FIG. 4 shows a housing component with front plate 155, as well as a further housing component configured as a housing channel 159. The drive unit 160 and the other components of the clamping device, such as the ramp loop 125 and the threaded plate 112, are arranged in the housing channel 159. This housing channel 159 can also be used as a mounting rail or be connected to a mounting rail. If the housing channel 159 is used as a mounting rail, additional masses can be fitted here. The masses to be fixed depend on the overall weight of the holding segment 102 to be attached or further holding segments connected thereto. Furthermore, it is not only the distal arm segments and possible intermediate joints which should be taken into account as mass, but rather also the distally attachable instruments. If the arm segments arranged and affixed or coupled on the distal end of the clamping device are extended horizontally, the greatest stress arises with regard to the clamping device, which must be taken into account when designing masses. For this horizontal position, a holding force of at least 5 kg must be made available.

The maximum force which the spindle 110 has to generate and the torque required for this can be selected, depending on the holding device or instrument which is coupled on, by a control unit or controller. Furthermore, the drive unit 160, i.e. the gear mechanism, can be selected depending on the application. Compared to the previously depicted embodiments, FIG. 4 additionally shows a sliding square 117, which connects the drive unit 160 to the spindle 110 which is only partly shown. Since, in the exemplary embodiment shown, the spindle 110 and the threaded plate are floatingly mounted and are able to move relative to the housing 150, the transmission of the torque from the drive unit 160 is performed by means of the sliding square 117. In this manner, the axial offset can be compensated. It is also possible for other equivalent tools to be used to compensate the axial offset.

The threaded spindle 110 runs in the threaded plate 112, with the inner thread being supported rearwardly by the forward movement of the spindle. This bearing force presses on the wedge body 131 via three sliding bodies designed as barrel-shaped rollers. The expansion wedge or wedge body 131 is situated mirror-symmetrically with all nine sliding bodies also underneath the spindle 110 (not shown in FIG. 4). Each wedge body 131 is laterally supported against the housing 150 via three sliding bodies. In contrast, the wedge body 131 in turn presses three sliding bodies onto an inclined surface of the ramp loop 125. This surface of the ramp loop 125 experiences a lateral tensile force as a result. The tightening path and the tightening force can be influenced by appropriately selecting the inclination of the wedge surfaces and associated ramp surfaces. This force is transmitted onto the cross-hole bolt 142 via a tightening screw not shown here.

The perpendicular base column or holding segment 101 is arranged in the cross-hole bolt 142. The base column or holding segment 101 can be clamped by the laterally acting tightening force. If the first holding segment is pulled to the housing 150 by the cross-hole bolt 142, it presses the column head 151 onto the housing wall or the wall of the housing channel and thus clamps the holding segment 101 or housing 150 against rotation.

Figure 5:
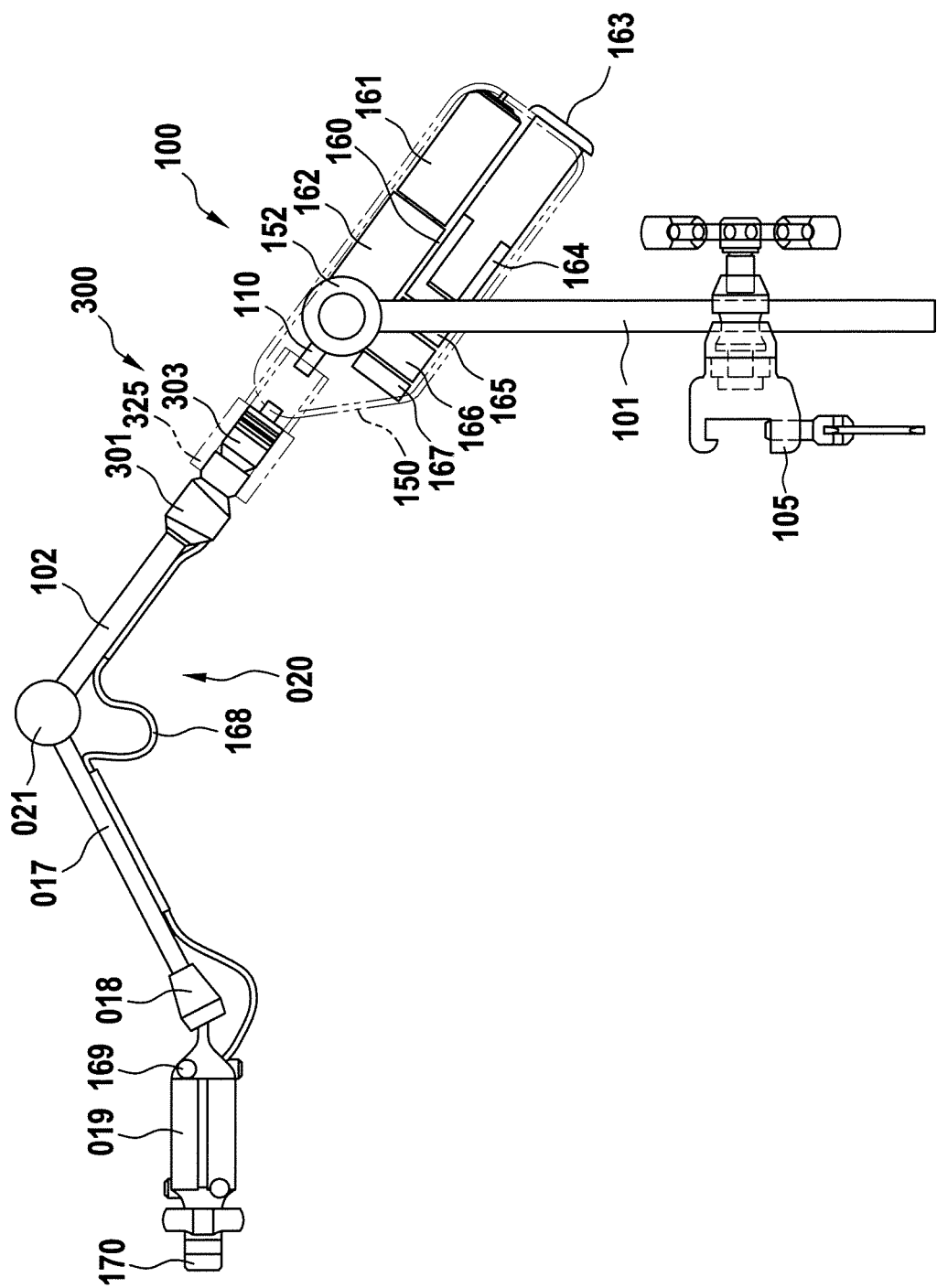
FIG. 5 shows a schematic view of a holding system with a further embodiment of the clamping device.

FIG. 5 shows a holding system with a clamping device 100 according to the invention. The first holding segment 101 is designed as a base column. This base column or the first holding segment 101 is intended to be compatible with all existing and commercially customary clamping units 105, so that it can be securely clamped to an operating table. For example, the base column or the first holding segment 101 can have a diameter of approximately 16 mm. Depending on a particularly large load capacity, larger diameters up to a maximum of 2 cm can also be provided. The clamping device 100 has a housing 150. For pivotability of the first holding segment or base column 101, there is located between the housing and the holding segment 101 a joint 152 which, due to the holding system or holding arm distally attached to the clamping device 100, can also be called a shoulder joint.

The affixing point of the clamping unit 105 for the first holding segment 101 is arranged in the proximal region of the clamping device 100. The proximal region can be located close to the floor or an operating table. The holding system can alternatively be ceiling-supported as opposed to an operating-table-supported system. The distal region of the holding system is the region which is remote from the proximal region. A holding device 20 in the form of a holding arm, with an upper arm and a lower arm respectively, is attached to the distal side of the clamping device through a coupling device 300. The attached holding device 20 comprises two holding segments 102 and 017, which are pivotably connected to one another by a central joint 21.

A handle 019 is attached to the distal holding segment 017. A medical instrument, for example, can be affixed to the free end of the handle 019 or holding system. For this purpose, the distal end of the handle 019 has a coupling unit 170. This coupling unit 170 can preferably be configured as a rapid-coupling unit such as the known KSLOCK interface. Various medical instruments such as microscissors, forceps, tweezers, punches or the like can be attached to such an autoclavable rapid-coupling unit 170. Accessories for the operation can also be provided, which can be affixed to the rapid-coupling unit. Thus, a hand rest, for example, can be coupled via the rapid-coupling unit 170. With such a hand rest, the operators can keep a steady hand during surgical interventions lasting several hours.

Alongside the connection to the hand joint 018 and the rapid-coupling unit 170, the handle has an actuation element 169. The drive unit 160 of the clamping device 100 can be activated by the distal actuation element 169. The control signal for the activation or actuation of the spindle 110 can be conducted to the drive unit 160 via the cable 168. The cable 168 is guided partly along the holding segments 017 and 102. The cable is guided, with some play, between the proximal holding segment 102 and the distal holding segment 117, so that the central joint 21 can move freely. Finally, the cable is guided partly in the interior of the holding segment 102 and in the depiction shown in FIG. 4, the cable enters the bolt element 301. The coupling device 300 has suitable contact elements inside it to further conduct the signal to the drive unit 160. As an alternative to the cable-guided activation, radio-controlled triggering of the clamping device is conceivable.

In the example depicted, the drive unit 160 includes, for the spindle 110, an electric motor 161 with a gear mechanism 162. The power is supplied to the drive unit 160 by a battery 163. The battery 163 is arranged in the battery shaft 164 and is controlled via the battery control unit 165. Furthermore, a drive control unit 166, as well as a switching logic 167, is located in the housing. The spindle 110 can be driven by means of the gear mechanism 162 of the electric motor 161.

Figure 6:
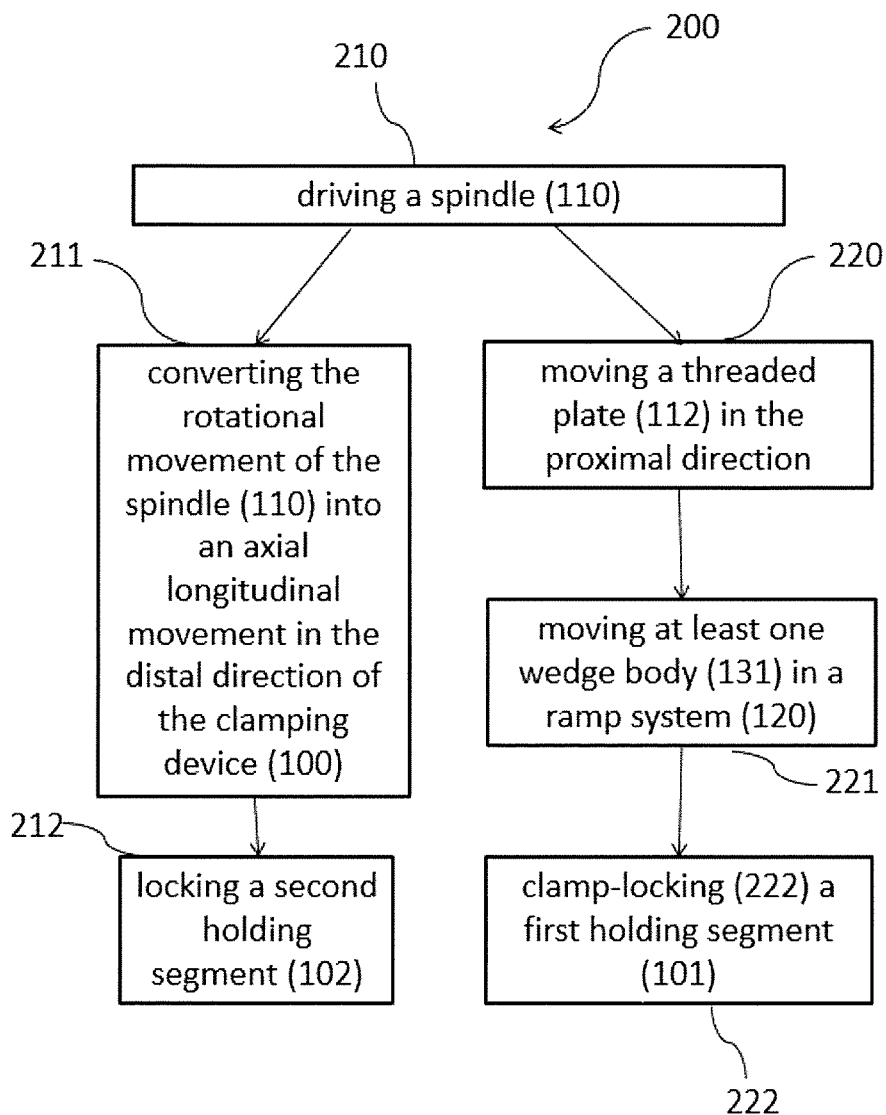
FIG. 6 shows a schematic method diagram for the locking of at least two holding segments by means of a clamping device according to the invention.

FIG. 6 shows a method 200 according to the present invention. 210, the driving of a spindle 110, is shown as a first method step. As a result of the driving of a spindle 110, two movements are initiated. On the one hand, in step 211, the rotational movement of the spindle 110 is converted into an axial longitudinal movement in the distal direction of the clamping device 100. With the aid of this conversion 211, a second holding segment 102 can be locked in a further step 212.

In the step 220, the moving of a threaded plate in the proximal direction takes place by the driving 210 of the spindle. As a result of the method step 220, at least one wedge body 131 is moved (221) in a ramp system 120. This step 221 is followed by the method step 222. This last step 222 in turn brings about a clamp-locking 222 of a first holding segment 101. The first holding segment 101 can be a base column here.

The invention claimed is:

1. A clamping device for human-medicine or veterinary-medicine applications for the frictionally engaged locking of at least two holding segments, comprising:
   a first holding segment,
   a driveable spindle, via which a rotational movement can be converted into an axial longitudinal movement for spindle-locking another holding segment,
   wherein a threaded plate can be moved in the opposite direction during the spindle movement,
   wherein, by counter-movement of the threaded plate, at least one wedge body is moveable in a ramp system, in order to clamp the first holding segment, and
   wherein the ramp system has at least one ramp loop which is penetrated centrally by the spindle and which has at least one ramp, in order to move the at least one wedge body laterally with respect to the spindle axis.

2. The clamping device according to claim 1, wherein a housing is pivotably borne around a transverse axis and around the axis of the first holding segment.

3. The clamping device according to claim 2, wherein the interengaging threads of the spindle and of the threaded plate are designed as a trapezoidal thread.

4. The clamping device according to claim 2, wherein the housing has a mounting rail for fitting additional masses.

5. The clamping device according to claim 1, wherein the threaded plate is arranged axially concentric with the spindle and has an inner thread which is mutually engaged with an outer thread of the spindle for displacement in the axial direction.

6. The clamping device according to claim 1, wherein the clamping device has a locking unit which interacts with the ramp system, for the clamping of the first holding segment,
   wherein the locking unit has a tightening screw, which can be moved transversely to the spindle axis by the ramp system, and a cross-hole bolt which guides the first holding segment.

7. The clamping device according to claim 6, wherein the ramp loop can be supported on one side by a support arranged in a stationary manner in the housing, in order to pull the cross-hole bolt, for the clamping, to the housing, or to push it away therefrom, by means of the tightening screw.

8. The clamping device according to claim 1, wherein the ramp loop has, respectively on two opposing sides, at least one ramp for interacting with assignable wedge bodies, in order to form two opposing ramp/mating-ramp systems.

9. The clamping device according to claim 1, wherein the at least one ramp and at least one mating ramp engage one another with assignable wedge surfaces of the wedge body, this engagement being brought about by a multiplicity of sliding bodies.

10. The clamping device according to claim 9, wherein the sliding bodies are rolling bodies in the form of spheres, cylinder rollers or barrel rollers.

11. The clamping device according to claim 9, wherein the at least one ramp and/or mating ramp have curved tracks for the sliding bodies.

12. The clamping device according to claim 1, wherein the at least one ramp and mating ramp directly engage in a sliding manner with assignable wedge surfaces of the wedge body.

13. The clamping device according to claim 1, wherein the spindle and/or the locking unit has a receptacle for receiving a spring.

14. The clamping device according to claim 1, wherein the spindle can be driven by a drive unit, the drive unit being selected from one of the group comprising an electric motor, a pneumatic drive and a hydraulic drive.

15. The clamping device according to claim 14, wherein the drive unit includes an electric motor and the spindle is floatingly mounted; and wherein a compensator is provided between the spindle and the electric motor, the compensator compensating an axial offset when transmitting torque from the electric motor.

16. A clamping device for human-medicine or veterinary-medicine applications for the frictionally engaged locking of at least two holding segments, comprising:
a first holding segment,
a driveable spindle, via which a rotational movement can be converted into an axial longitudinal movement for spindle-locking another holding segment,
wherein a threaded plate can be moved in the opposite direction during the spindle movement,
wherein, by counter-movement of the threaded plate, at least one wedge body is moveable in a ramp system, in order to clamp the first holding segment,
wherein the clamping device has a locking unit which interacts with the ramp system, for the clamping of the first holding segment, and
wherein the locking unit has a tightening screw, which can be moved transversely to the spindle axis by the ramp system, and a cross-hole bolt which guides the first holding segment.

17. The clamping device according to claim 16, wherein the ramp loop can be supported on one side by a support arranged in a stationary manner in the housing, in order to pull the cross-hole bolt, for the clamping, to the housing, or to push it away therefrom, by means of the tightening screw.

18. The clamping device according to claim 16, wherein the ramp system has at least one ramp loop, which is penetrated centrally by the spindle and which has, respectively on two opposing sides, at least one ramp for interacting with assignable wedge bodies, in order to form two opposing ramp/mating-ramp systems.

* * * * *